73-633 SR

9/17/85 XR 4,541,434

United States Patent [19]

Okado

[11] Patent Number: 4,541,434

[45] Date of Patent: Sep. 17, 1985

[54] ULTRASONIC SCANNING APPARATUS

[75] Inventor: Takeshi Okado, Tochigi, Japan

[73] Assignee: Tokyo Shibaura Denki Kabushiki Kaisha, Kawasaki, Japan

[21] Appl. No.: 510,305

[22] Filed: Jul. 1, 1983

[30] Foreign Application Priority Data

Jul. 2, 1982 [JP] Japan ................................ 57-113856

[51] Int. Cl.[4] ................................................ A61B 10/00

[52] U.S. Cl. .................................... 128/660; 128/661; 73/633

[58] Field of Search .................. 128/660, 661; 73/629, 73/633, 634

[56] References Cited

U.S. PATENT DOCUMENTS

| | | | |
|---|---|---|---|
| 4,151,834 | 5/1979 | Sato et al. | 128/660 |
| 4,185,501 | 1/1980 | Proudian et al. | 128/660 |
| 4,241,611 | 12/1980 | Specht et al. | 128/660 |
| 4,246,791 | 1/1981 | Glenn | 128/660 |
| 4,274,421 | 6/1981 | Dory | 128/660 |
| 4,282,879 | 8/1981 | Kunii et al. | 128/660 |
| 4,330,874 | 5/1982 | Sorwick | 128/660 |
| 4,418,698 | 12/1983 | Dory | 73/633 |

FOREIGN PATENT DOCUMENTS

| | | | |
|---|---|---|---|
| 2040451 | 8/1980 | United Kingdom . | |
| 2067759 | 7/1981 | United Kingdom | 128/660 |

*Primary Examiner*—Kyle L. Howell
*Assistant Examiner*—Ruth S. Smith
*Attorney, Agent, or Firm*—Cushman, Darby & Cushman

[57] ABSTRACT

An ultrasonic scanning apparatus has a housing which includes the apparatus which has a cylindrical body extending along a central axis thereof and a window at a distal end of the cylindrical body. A transducer is disposed in the vicinity of the window to transmit an ultrasonic beam in a direction perpendicular to the central axis of the housing, and a reflecting member is disposed to guide the ultrasonic beam to the outside through the window. A continuously rotating motor is disposed such that an output shaft thereof is parallel to the central axis of the housing. A swinging mechanism is coupled to the output shaft of the motor so as to swing the reflecting member within a predetermined angular range.

6 Claims, 7 Drawing Figures

ULTRASONIC SCANNING APPARATUS

BACKGROUND OF THE INVENTION

The present invention relates to an ultrasonic scanning apparatus having: a housing with a window through which an ultrasonic beam passes; a transducer fixed in the housing and having an ultrasonic transmitting/receiving surface for transmitting/receiving the ultrasonic beam; a reflecting member opposing the ultrasonic transmitting/receiving surface so as to form an angle therebetween, the reflecting member serving to reflect the beam from the ultrasonic transmitting/receiving surface so as to deliver the ultrasonic beam through the window; driving means for driving the reflecting member to change the propagation direction of the ultrasonic beam reflected by the reflecting member; and a motor having an output shaft coupled to the driving means.

The ultrasonic scanning apparatus of this type has been used in an ultrasonic diagnostic apparatus for performing tomogram so as to examine a part of the patient's body and form a tomogram thereof. In general, in order to obtain a tomogram of the heart or the like, the heart must be scanned with an ultrasonic beam from outside the body through a narrow space between adjacent ribs.

A typical example of a conventional ultrasonic scanning apparatus is illustrated in FIGS. 1 and 2. In this ultrasonic scanning apparatus, an ultrasonic beam is generated by a transducer. The ultrasonic beam is then projected from the transducer onto an ultrasonic reflecting mirror which is mechanically pivotable. The propagation direction of the ultrasonic beam is changed over time and the ultrasonic beam irradiates the portion of the patient's body to be examined, thereby performing mechanical sector scanning.

FIGS. 1 and 2 show a conventional ultrasonic scanning apparatus 10. A housing 12 of the apparatus 10 comprises a cylindrical portion 14 and a sector-shaped portion 16. The sector-shaped portion 16 extends in a direction substantially perpendicular to the central axis of the cylindrical portion 14. The sector-shaped portion 16 has an arc-shaped outer portion (i.e., an arcuated portion) 18. An arc-shaped window 20 is formed in the arcuated portion 18 and effectively transmits the ultrasonic beam therethrough. A partition wall 22 is formed in the cylindrical portion 14. The sector-shaped portion 16 extends downward from the part of the cylindrical portion 14 which is located to the left (FIG. 1) of the partition wall 22. A transducer 24 is mounted on the left end portion (FIG. 1) of the cylindrical portion 14 through a damper member 26 such that an ultrasonic transmitting/receiving surface 35 is perpendicular to the central axis of the cylindrical portion 14. A motor 28 and an angle detector 30 are mounted in the right-hand part (FIG. 1) of the cylindrical portion 14. The angle detector 30 is connected to the motor 28. An output shaft 32 of the motor 28 extends toward the transducer 24 through a bearing 34 and a seal member 36 so as to be coaxial with the central axis of the cylindrical portion 14. The bearing 34 and the seal member 36 are mounted in the partition wall 22. The seal member 36 prevents an ultrasonic propagation medium 38 (e.g., water containing a rustproof agent) in the sector-shaped portion 16 from leaking to the motor 28 through the seal member 36. A reflector (e.g., a mirror) 42 is rotatably disposed at the distal end of the output shaft 32 such that its reflecting surface 40 is inclined by a predetermined angle (45° in FIG. 1) with respect to the ultrasonic transmitting/receiving surface 35.

When the transducer 24 and the motor 28 are powered, the ultrasonic beam from the transducer 24 is reflected by the rotating mirror 42, so that the ultrasonic beam is continuously rotated in one direction upon rotation of the mirror 42 in a plane substantially perpendicular to the central axis of the cylindrical portion 14. The mirror 42 is substantially perpendicular to the surface of drawing (FIG. 1) and its reflecting surface 40 is inclined to face the lower left corner. The ultrasonic beam reflected by the mirror 42 is reflected downward (FIG. 1) into the patient's body through the window 20 and a body surface 44. Therefore, the inside of the body is sector-scanned for an angular range determined by the size of the window 20. The ultrasonic beam transmitted into the body is reflected by the object to be examined and is received by the transducer 24 in a direction opposite to the forward propagation direction. The transducer 24 generates an electric signal which provides information about the inside of the body. This signal is supplied to an external electric device (not shown) for diagnosis of the inside of the body and reconstruction of a tomogram. A propagation path 46 has a width indicated by the alternate long and two dashed lines in FIG. 1. The ultrasonic beam is transmitted by the transducer 24 and is projected outside through the window 20 along the propagation path 46.

FIG. 2 is a sectional view of a structure taken along the line 2—2 in FIG. 1 when transducer 24, damper element 26 and housing 12 are partially eliminated from the apparatus 10 (FIG. 1) for illustrative convenience. Referring to FIG. 2, the ultrasonic beam can be projected through the window 20 disposed at the distal end of the sector-shaped portion 16 within a possible angular range $W_1$. In fact, the ultrasonic beam is projected into the body between adjacent ribs 48 within an angular range $W_2$.

The conventional apparatus 10 is very effective for ultrasonic diagnosis and tomogram reconstruction. However, strong demands for further improvements have arisen. First, since the cylindrical portion 14 extends perpendicularly to the sector-shaped portion 16 which is brought into tight contact with the body surface 44, an inclined angle of the distal end of the sector-shaped portion 16 with respect to the body surface 44 is greatly limited. Referring to FIG. 1, for example, when an operator such as a doctor wishes to project the ultrasonic beam from the upper right corner to the lower left corner and rotates the apparatus 10 clockwise, the cylindrical portion 14 extending to the right abuts against the body surface 44. A small angle with respect to the body surface 44 can not be obtained, resulting in inconvenience. When the doctor uses the apparatus 10 in a clinical examination, he searches for the object to be examined while watching the tomogram of the inside of the body. The doctor then moves and orients the sector-shaped portion 16 so as to precisely examine the desired object in different directions and angles. However, in the conventional apparatus 10, the inclined angle of the sector-shaped portion 16 with respect to the body surface 44 is limited as described above. In order to eliminate this drawback, it has been proposed that the length of the sector-shaped portion 16 be increased so as to increase the distance between the body surface 44 and the cylindrical portion 14. However, the size of the apparatus 10 is then increased and the scanning angular range is decreased, resulting in inconvenience. It should be noted that the decrease in the scanning angular range is apparent from FIG. 2. More particularly, when the sector-shaped portion 16 is increased in length in FIG. 2, the distance between the mirror 42 and the window 20 is increased. As a result, the possible angular range $W_1$ is decreased. Along with this, since the distance between the mirror 42 and the ribs 48 is increased, the range $W_2$ is also decreased.

Second, the distance between the mirror 42 and the window 20 is increased because of the presence of the sector-shaped portion 16. Therefore, the ranges $W_1$ and $W_2$ are restricted in practice.

Third, although the ultrasonic beam reflected by the mirror 42 is rotated through 360° upon continuous rotation of the motor 28, ultrasonic beams reflected in any direction other than directions falling within the range $W_1$ cannot contribute to sector scanning.

In order to eliminate these drawbacks, a method was proposed to periodically reverse the rotational direction of the motor 28 so as to swing the mirror 42 within the range $W_1$ (FIG. 2). This leads to complex construction and control.

SUMMARY OF THE INVENTION

It is an object of the present invention to provide an ultrasonic scanning apparatus which eliminates the drawbacks of the conventional ultrasonic scanning apparatus, which has a structure for projecting an ultrasonic beam from various directions onto an object to be examined, and which allows projection of all the transmitted ultrasonic beams onto the object to be examined.

In order to achieve the above object of the present invention, there is provided an ultrasonic scanning apparatus wherein (1) a cylindrical housing for storing the entire apparatus therein extends along the central axis thereof and has a window at the distal end thereof, (2) a swinging mechanism is used in a driving means to swing a reflecting member within a predetermined angular range, and (3) a motor has an output shaft disposed substantially parallel to an ultrasonic transmitting/receiving surface.

The following effect can be obtained by the ultrasonic scanning apparatus of the present invention which has features indicated by items (1), (2) and (3) described above. Since the housing is formed as indicated by item (1), the ultrasonic beams can be easily projected through the window at the distal end of the housing to a given projection point on the body surface in various directions and at various angles. Furthermore, since the reflecting member swings as indicated by item (2), all the ultrasonic beams transmitted from the transducer can be used for sector scanning, thereby providing effective operation. In addition to these effects, since the output shaft of the motor extends perpendicularly to the ultrasonic beam from the oscillator, as indicated by item (3), the transducer and the reflecting member can be disposed in the vicinity of the window in consideration of the motor position. Therefore, the angular range of sector scanning can be increased. Furthermore, since the transducer is fixed in the housing, the electric wires connected to the transducers do not move in practice even though the reflecting member swings. Along with the above effects, disconnections can not occur, nor can the connecting portions become removed.

According to a preferred embodiment of the present invention, the positional relationship of the swinging mechanism for swinging the reflecting member upon continuous rotation of the motor, the construction of the output shaft of the motor so as to drive the swinging mechanism, and the construction of the reflecting member driven by the swinging mechanism will be as described below. The motor is disposed with respect to the reflecting member such that the central axis of the output shaft of the motor crosses the central axis of the reflecting member so as to form an orthogonal intersection. The swinging mechanism comprises a rotary arm mounted at the distal end of the output shaft so as to substantially radially extend therefrom, and a fork member rotatably supported at the distal end of the rotary arm. The fork member comprises a handle rotatably supported at the distal end of the rotary arm so as to extend toward the orthogonal intersection, and a U-shaped portion which is mounted at the distal end of the handle and which has two arms supporting the two sides of the reflecting member.

More particularly, the two arms rotatably support the two sides of the reflecting member at two ends of a line extending through the reflecting member such that the line passes through the intersection and is perpendicular to the handle. When the swinging mechanism is driven by the motor, the fork member is rotated around the output shaft of the motor, using the orthogonal intersection as a fixed point, thereby performing a precession movement. Therefore, the reflecting member swings between two directions through a predetermined angular range. This swinging mechanism has a simple construction and is mechanically operated. The swinging mechanism thus does not require a special controlling means. Furthermore, the mirror can be swung stably and properly upon swinging of the reflecting member.

DETAILED DESCRIPTION OF THE PREFERRED EMBODIMENT

Figure 1:
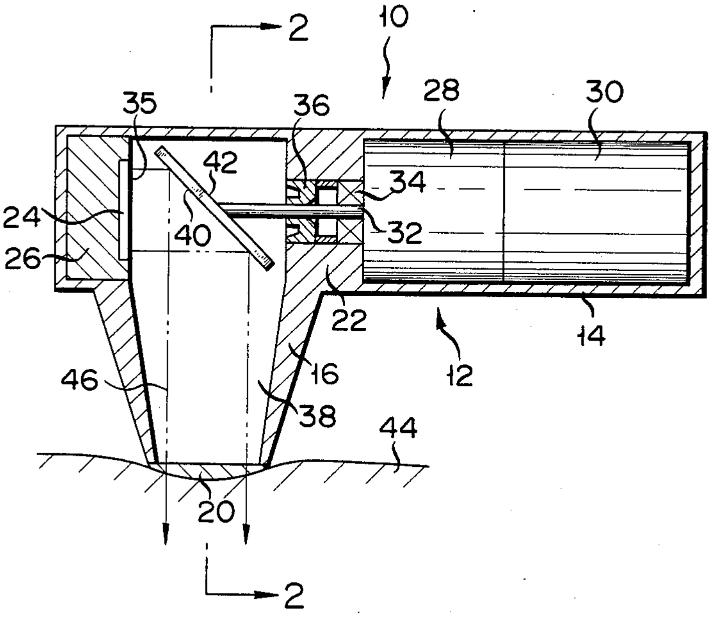
FIG. 1 (PRIOR ART)
FIG. 1 is a partial sectional front view of a conventional ultrasonic scanning apparatus.

An ultrasonic scanning apparatus according to an embodiment of the present invention will be described with reference to FIGS. 3, 4 and 5. The same reference numerals as used in the conventional apparatus shown in FIGS. 1 and 2 denote similar members in FIGS. 3, 4 and 5. A housing 52 of an ultrasonic scanning apparatus 50 of the present invention shown in FIG. 3 comprises a circular or elliptical cylinder extending along the central axis C—C (longitudinal direction thereof). An electric cable 54 leading from one end (i.e., the upper portion in FIG. 3) of the housing 52 is connected to a proper power supply (not shown). A window 58 is formed at the other end (i.e., the lower portion in FIG. 3) of the housing 52 so as to transmit an ultrasonic beam therethough. The window 58 has a predetermined width along the right-to-left direction in FIG. 3, and is formed perpendicular to the surface of the drawing. A partition wall 22 is formed in the housing 52 to be substantially perpendicular to the central axis C—C. A motor 28 and an angle detector 30 coaxial therewith are disposed above the partition wall 22 such that an output shaft 32 of the motor 28 extends downward through the partition wall 22 substantially perpendicular thereto. A bearing 34 and a seal member 36 are mounted in the partition wall 22. The output shaft 32 of the motor 28 extends through the bearing 34 and the seal member 36.

A space (i.e., an ultrasonic beam generating chamber) 60 is formed below the partition wall 22 of the housing 52 and is filled with a medium 38 for effectively propagating the ultrasonic beam. An ultrasonic transducer 24 is mounted on the partition wall 22 through a damper 26 such that an ultrasonic transmitting/receiving surface 35 of the transducer 24 is substantially parallel to the central axis C—C. The damper 26 damps the ultrasonic beam component propagating in a direction opposite to the transmitting/receiving surface 35 so as to allow the transmitting/receiving surface 35 to deliver an ultrasonic beam having a proper waveform. The medium 38 generally consists of water containing a proper rust-proof agent mixed therein. The medium 38 is prevented from leaking into the motor 28 by the seal member 36. A support member 64 is disposed in the ultrasonic beam generating chamber 60 so as to extend downward from the partition wall 22. A mirror rotating shaft 66 opposed and substantially perpendicular to the transmitting-/receiving surface 35 of the transducer 24 is supported by the support member 64. The positional relationship among the output shaft 32 of the motor 28, the mirror rotating shaft 66 and the transducer 24 are set such that the central axis of the mirror rotating shaft 66 passes substantially through a center 68 of the transmitting-/receiving surface 35 of the transducer 24, and such that the central axis of the output shaft 32 of the motor 28 is substantially perpendicular to the central axis of the mirror rotating shaft 66. A point at which the central axes of the output shaft 32 and the mirror rotating shaft 66 cross is called an intersection 70. A reflecting member 72 for reflecting the ultrasonic beam is mounted on an end of the mirror rotating shaft 66 which opposes the transducer 24. The reflecting member 72 has a mirror 76 and a cylindrical boss 78 extending from the mirror 76 in a direction away from the transducer 24. The mirror 76 has a reflecting surface 74 which is inclined by an angle of about 45° with respect to the transmitting-/receiving surface 35 of the transducer 24. Referring to FIG. 3, the mirror 76 is positioned substantially perpendicular to the surface of the drawing (FIG. 3), and the reflecting surface 74 faces the lower left corner. This position of the reflecting member 72 is called a reference position. The output shaft 32 of the motor 28 is coupled to the reflecting member 72 through a swinging mechanism 80. The swinging mechanism 80 is mounted at the distal end of the output shaft 32. The swinging mechanism 80 comprises a substantially radially extending rotary arm 82 and a fork member 84 rotatably supported at the extended end of the rotary arm 82. The rotary arm 82 extends parallel to the surface of the drawing (FIG. 3). FIG. 4 shows a detailed construction of the swinging mechanism 80 in a state wherein the swinging mechanism 80 is slightly rotated counterclockwise as viewed from the top. This state corresponds to the state wherein the main part of the swinging mechanism 80 is viewed from the left side and the motor 28 and the mirror 76 are omitted. The fork member 84 is rotatably supported at the extended end of the rotary arm 82. The fork member 84 is constituted by a U-shaped portion 90 and a handle 86 extending toward the intersection 70. The U-shaped portion has two arms 88 for rotatably supporting the reflecting member 72 at corresponding positions to be described below. The positions at which the arms 88 are coupled to the two sides of the boss 78 are two ends $D_1$ and $D_2$ of a diameter 94 which is substantially perpendicular to the handle 86 within a section 92 (indicated by the alternate long and two short dashed line). The section 92 is perpendicular to the central axis $X_2$—$X_2$ of the mirror rotating shaft 66 and includes the intersection 70 between the central axis $X_1$—$X_1$ of the output shaft 32 and the central axis $X_2$—$X_2$.

Figure 3:
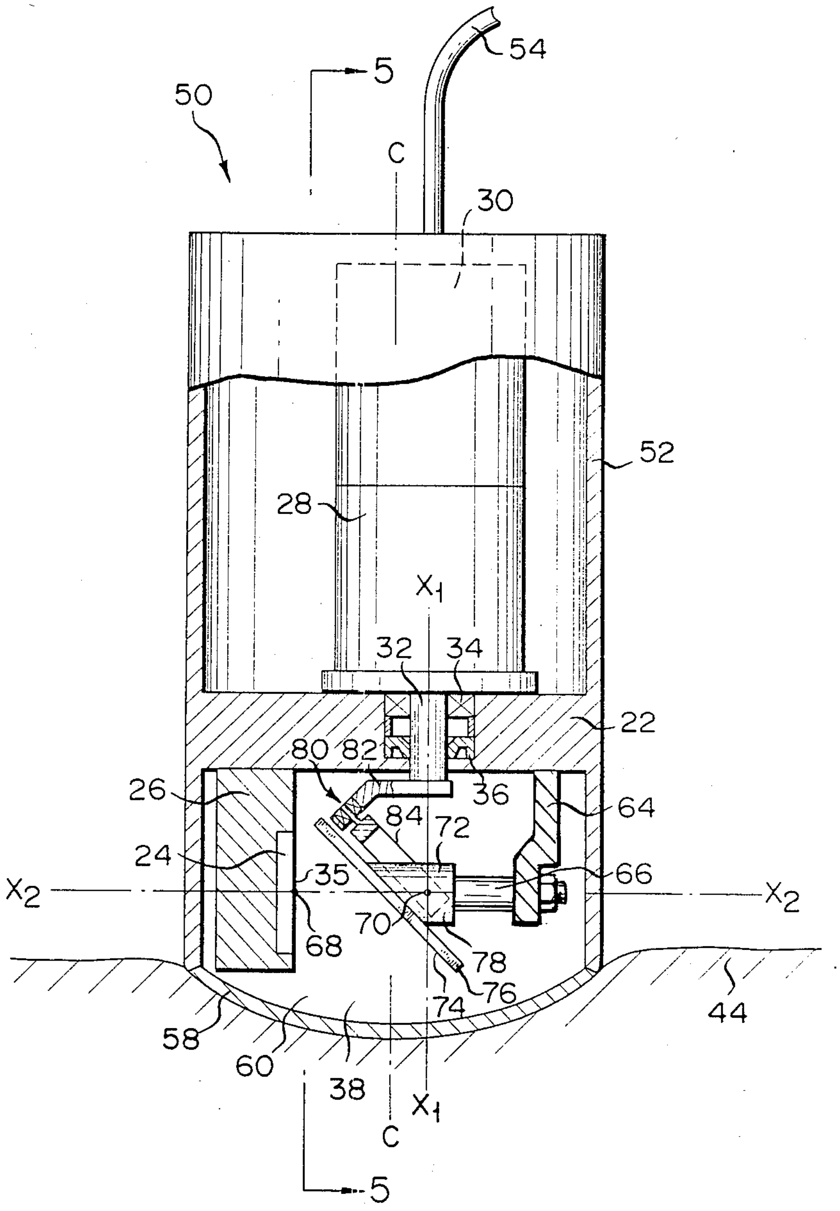
FIG. 3 is a partial sectional front view of an ultrasonic scanning apparatus according to an embodiment of the present invention.
Figure 4:
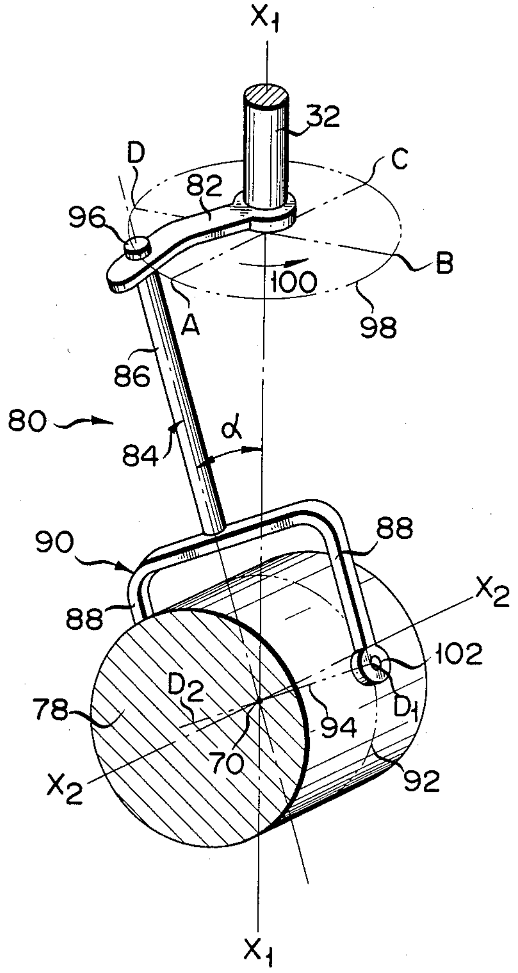
FIG. 4 is a perspective view showing the main part of a swinging mechanism of the apparatus shown in FIG. 3.

Referring to FIG. 4, when the motor 28 (not shown) is driven to rotate the rotary arm 82 counterclockwise when viewed from the top, a vertex 96 of the handle 86 (the length of handle 86 is drawn enlarged with respect to the scale of FIG. 3 so as to be more clear) is moved to pass points A, B, C and D and trace a track 98 indicated by the alternate long and two short dashed line. The points A and C correspond to two ends of a diameter, which is substantially parallel to the central axis $X_2$—$X_2$, of the track 98. The points B and D correspond to two ends of another diameter substantially perpendicular to the above diameter.

Since the output shaft 32 is coupled to the boss 78 of the reflecting member 72 with the positional relationship as shown in FIG. 4, upon rotation of the output shaft 32 in a direction indicated by an arrow 100, the boss 78 and the mirror 76 (FIG. 3) mounted thereon swing from left to right and vice versa in accordance with the central axis $X_2$—$X_2$ as a center of a given angular range. The swinging operation will be described in detail hereinafter. Referring to FIG. 4, when the vertex 96 of the handle 86 reaches the point A the handle 86 takes a front-facing position, while maintained at an angle $\alpha°$ with respect to the central axis $X_1$—$X_1$. The diameter 94 is substantially perpendicular to the central axes $X_1$—$X_1$ and $X_2$—$X_2$. Under this condition, the reflecting member 72 is located at the reference position as indicated in FIG. 3. When the vertex 96 of the handle 86 is moved from the point A to the point B, the handle 86 is gradually inclined and is moved toward the back (FIG. 4). The diameter 94 is accordingly rotated clockwise viewed from the $X_2$—$X_2$ direction and from the front side of FIG. 4). When the vertex 96 has reached the point B, the handle 86 is inclined to the right (FIG. 4) by the angle $\alpha°$ with respect to the central axis $X_1$—$X_1$. The reflecting member 72 is inclined by the angle $\alpha°$ in the clockwise direction with respect to the reference position upon movement of the boss 78. In the same manner as described above, when the vertex 96 has reached the point C, the diameter 94 and hence the reflecting member 72 return to the position where the vertex 96 is located at the point A, except that the handle 86 is inclined toward the back by the angle $\alpha°$. Similarly, when the vertex 96 is moved to the point A through the point D, the handle 86 passes along the track 98 and returns to the reference point. During this operation, the reflecting member 72 is rotated counterclockwise by the angle $\alpha°$ and is then rotated clockwise by the angle $\alpha°$, so that the reflecting member 72 returns to the reference position. Meanwhile, the handle 86 is rotated toward the front (FIG. 4) through an angle $2\alpha°$ and returns to the reference position. In this manner, the reflecting member 72 swings by the angle $\alpha°$ to the right or left with respect to the reference position upon continuous rotation of the motor 28. As a result, the ultrasonic beam from the oscillator 24 is swung to perform sector scanning within the angle $\alpha°$ with respect to the reference point in each of the right and left directions. When the ultrasonic beam reflected from inside the patient's body is incident on the transducer 24, the transducer 24 generates an electric signal having an amplitude corresponding to the intensity of the reflected ultrasonic beam. The angle detector 30 generates an electric signal indicating the direction of the mirror 76. These signals are supplied to an external electric circuit through the electric cable 54 and are used for ultrasonic diagnosis and reconstruction of a tomograph.

Figure 5:
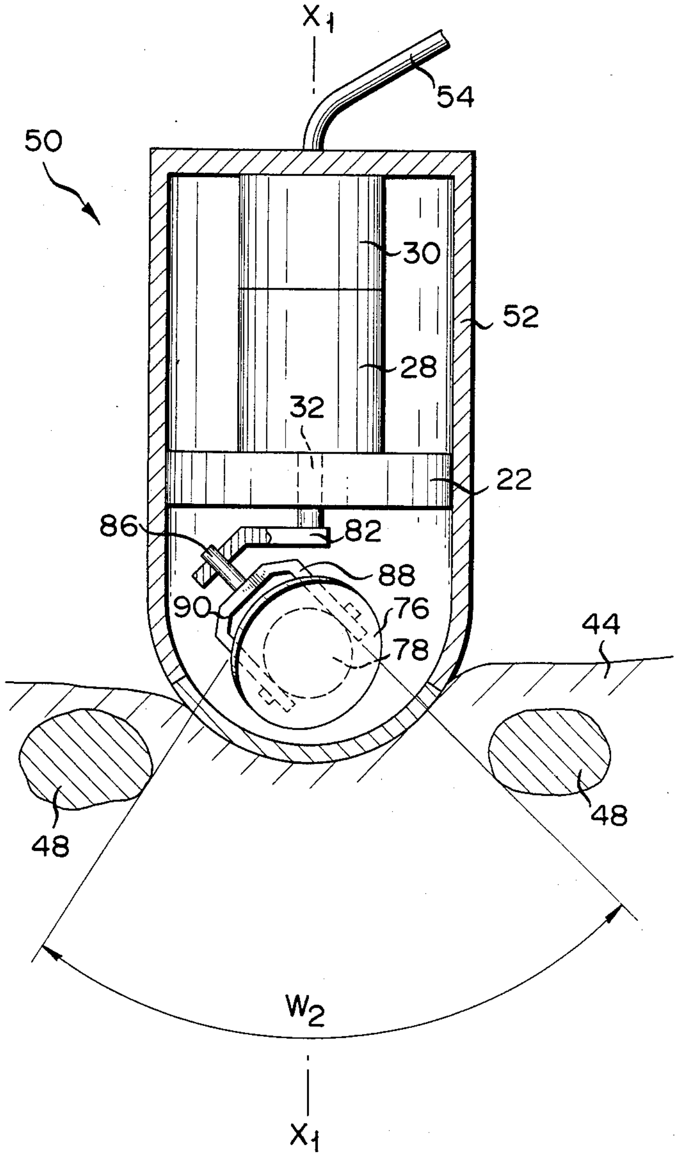
FIG. 5 is a side view showing a section of the apparatus in FIG. 3 taken along the line 5—5 therein.

FIG. 5 is a sectional view of the apparatus 50 taken along the line 5—5 in FIG. 3. In the swinging mechanism 80, the vertex 96 of the handle 86 is located at the point D (FIG. 4). Therefore, the rotary arm 82 extends to the left (FIG. 5), and the mirror 76 mounted on the reflecting member 72 is rotated counterclockwise by the angle $\alpha°$ from the position corresponding to the reference position. FIG. 5 shows the state wherein the apparatus 50 is urged against the body surface 44, and an ultrasonic beam is projected between adjacent ribs 48 so as to perform sector scanning within the angular range $W_2$.

Figure 2:
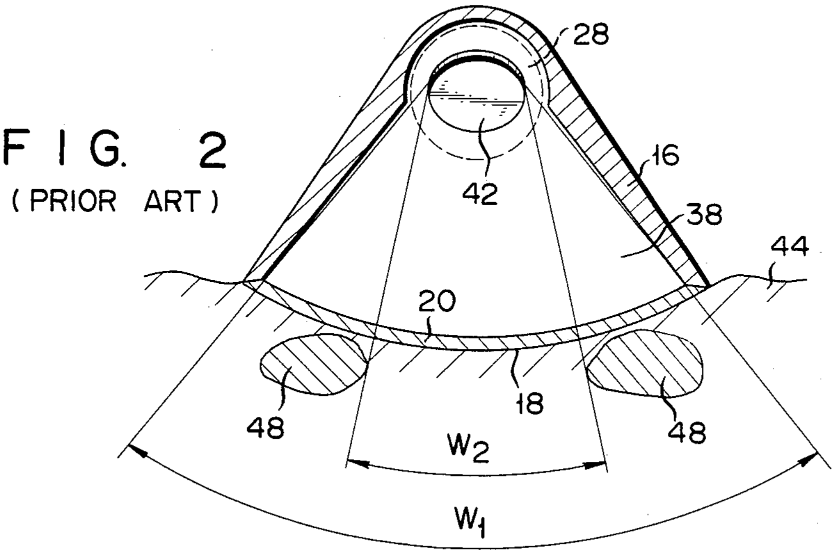
FIG. 2 (PRIOR ART)
FIG. 2 is a sectional view of the apparatus in FIG. 1 taken along the line 2—2 therein.
Figure 6A:
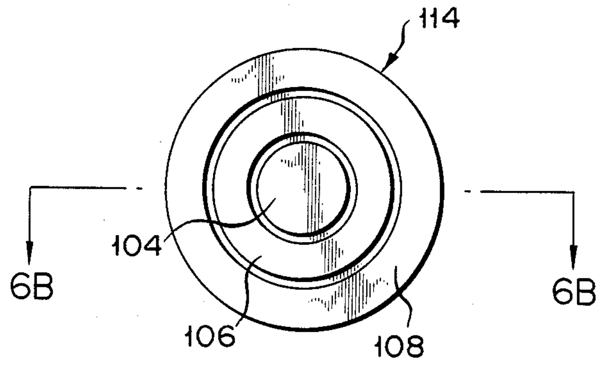
FIG. 6A is a front view of an annular array oscillator.
Figure 6B:
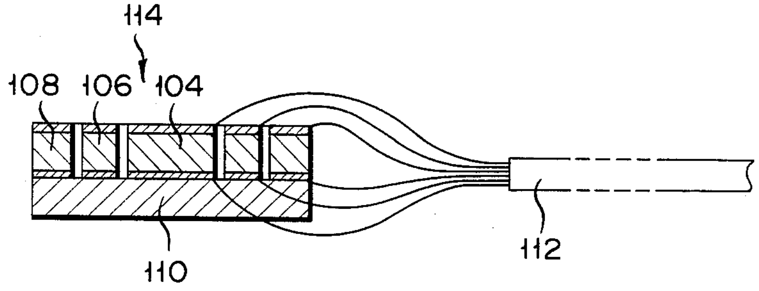
FIG. 6B is a sectional view of the annular array oscillator in FIG. 6A taken along the line 6B—6B therein.

In the above description, the type of transducer 24 which is used is not described. Various types of transducers may be used in accordance with a given ultrasonic diagnosis and a given reconstruction of a tomogram to be performed. In general, the transducer shown in FIGS. 1 and 3 is used. This transducer has a single ultrasonic transmitting/receiving disc. Another typical example of the transducer is an annular array transducer. As shown in FIGS. 6A and 6B, an annular array transducer 114 comprises a plurality of annular piezo-electric elements and a piezo-electric disc. The annular piezo-electric elements are concentrically arranged around the piezo-electric disc. The annular array transducer 114 shown in FIGS. 6A and 6B comprises a single piezo-electric disc 104, two annular piezo-electric elements 106 and 108, a backing 110 on which the piezo-electric disc 104 and the annular piezo-electric elements 106 and 108 are mounted, and an electric wiring 112 (not shown in FIG. 6A). In the annular array transducer 114, the timings of pulse signals applied to the piezo-electric disc 104 and the piezo-electric elements 106 and 108 are properly controlled so as to move the focal point of the ultrasonic beam generated from the transducer 114. The piezo-electric disc 104 and the piezo-electric elements 106 and 108 are driven to generate a high-intensity ultrasonic beam at the time of transmission. However, in the case of receiving the ultrasonic beam reflected from inside the patient's body, the piezo-electric disc 104 alone or the piezo-electric disc 104 and the piezo-electric element 106 adjacent thereto are driven to make the receiving aperture small. As a result, the condition of the inside of the patient's body can be examined with high resolution. The transducer having the single piezoelectric disc shown in FIG. 3 is called a single transducer as opposed to the annular array transducer.

When the ultrasonic scanning apparatus 50 of the above embodiment is used, the following advantages can be obtained. First, the ultrasonic beam can be projected through the window into the patient's body along any direction and at any inclined angle with respect to the body surface 44 of the patient. This can be achieved by a simple cylindrical construction (FIG. 3) that presents no obstacle even when the apparatus 50 is inclined at a small angle with respect to the body surface 44 so as to project the ultrasonic beam from the distal end thereof. Second, the angular range for sector scanning is increased. As described in the first advantage, the apparatus 50 has a simple cylindrical shape and need not be provided with the sector-shaped portion which extends transversely from the cylindrical body and which is disposed in the conventional apparatus. Therefore, the transducer 24 and the mirror 76 can be disposed in the vicinity of the window 58. An angular range of sector scanning with respect to the center of the mirror 76 (i.e., a possible range for sector scanning) is increased. Furthermore, the angular range within which the ultrasonic beam can be projected between adjacent ribs is, of course, increased in comparison with the case of the conventional apparatus. Third, all the ultrasonic beams generated by the transducer 24 are used for sector scanning. The ultrasonic beams may not be reflected by the reflecting member 72 in any direction other than directions falling within the range of the window 58. In order to achieve this, the transducer 24 is fixed, while the reflecting member 72 swings in the above embodiment. The reflecting member 72 and hence the mirror 76 can be swung by the swinging mechanism 80 disposed between the continuously rotating motor 28 and the reflecting member 72. Therefore, the swinging of the reflecting member 72 can be achieved with a compact construction and without using an electric controlling means or any other complicated mechanism which periodically reverses the motor rotation. Fourth, since the transducer 24 is fixed and the mirror 76 swings, the electric cable (not shown) connected to the transducer 24 may not become disconnected, thus eliminating electrical problems. Conventionally, when the transducer swings, the electric cable is tautened or loosened to frequently disconnect the electric cable. However, since the transducer 24 of the apparatus shown in FIG. 3 is fixed, such an accident does not occur. The fourth advantage is particularly useful when the annular array transducer 114 shown in FIGS. 6A and 6B is used since the array transducer 114 requires a plurality of connections. If the transducer 114 swings, disconnections tend to occur.

What is claimed is:

1. An ultrasonic scanning apparatus comprising:

a housing of generally cylindrical shape extending along a first axis thereof, said housing having an ultrasonic energy transmissive window at a first end thereof;

a motor means, disposed in said housing, for continuously rotating an output shaft thereof elongated toward said window along said first axis;

supporting member means disposed between said motor means and said window for swingably holding a mirror rotating shaft elongated along a second axis perpendicular to said first axis;

a swinging means, coupling said output shaft of said motor means with said mirror rotating shaft, for converting the continuous rotation of said output shaft into a swinging motion of said mirror rotating shaft, said swinging means having an arm with a first arm end connected to the motor output shaft so as to rotate therewith, and a fork member having a first end pivotably mounted to a second end of the arm and a second end journaled to the mirror rotating shaft to be rotatable to a third axis which passes said first and second axes at right angles to the said second axis the movement of said fork member defining a cone;

an ultrasonic reflector attached on an end of said mirror rotating shaft at an acute angle to the transmissive window; and transducer means, opposite to said reflector, for projecting an ultrasonic beam toward said reflector along said second axis, said reflector reflecting said ultrasonic beam toward said window, the beam being steered in a sector plane perpendicular to said second axis.

2. An apparatus according to claim 1, wherein the transducer means comprises a single transducer.

3. An apparatus according to claim 1, wherein the transducer means comprises an annular array transducer.

4. An apparatus according to claim 1, further comprising an angle detector, coupled to the motor means and disposed at the other end of the housing for detecting a rotation speed of the motor means.

5. The apparatus according to claim 1 wherein the arm is slightly bent so that the fork member in the conical rotation falls at right angles to the arm.

6. The apparatus according to claim 1 wherein the fork member includes a U-shaped arm journaled to both sides of the swinging shaft.

* * * * *